(12) United States Patent (10) Patent No.: US 8,121,858 B2
Friedlander et al. (45) Date of Patent: Feb. 21, 2012

(54) OPTIMIZING PHARMACEUTICAL TREATMENT PLANS ACROSS MULTIPLE DIMENSIONS

(75) Inventors: Robert R. Friedlander, New Haven, CT (US); Joanna Lynn Fueyo, Brighton, MA (US); Richard A. Hennessy, Austin, TX (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 995 days.

(21) Appl. No.: 12/054,074

(22) Filed: Mar. 24, 2008

(65) Prior Publication Data

US 2009/0240523 A1 Sep. 24, 2009

(51) Int. Cl.
 *G06Q 10/00* (2006.01)
 *G06Q 50/00* (2006.01)
(52) U.S. Cl. ............................... 705/2; 705/3
(58) Field of Classification Search .................. 705/2–4
 See application file for complete search history.

(56) References Cited

U.S. PATENT DOCUMENTS

| | | | |
|---|---|---|---|
| 4,328,978 A | 5/1982 | McLaughlin | |
| 6,058,391 A | 5/2000 | Gardner | |
| 6,189,004 B1 | 2/2001 | Rassen et al. | |
| 6,385,604 B1 | 5/2002 | Bakalash et al. | |
| 6,509,898 B2 | 1/2003 | Chi et al. | |
| 6,578,043 B2 | 6/2003 | Nye | |
| 6,629,106 B1 | 9/2003 | Narayanaswamy et al. | |
| 2002/0059183 A1 | 5/2002 | Chen | |
| 2002/0099691 A1 | 7/2002 | Lore et al. | |
| 2002/0099692 A1 | 7/2002 | Shah et al. | |
| 2002/0147617 A1* | 10/2002 | Schoenbaum et al. | 705/4 |
| 2002/0156791 A1 | 10/2002 | Nesamoney et al. | |
| 2002/0184225 A1 | 12/2002 | Ghukasyan | |
| 2003/0074222 A1 | 4/2003 | Rosow et al. | |
| 2003/0088438 A1 | 5/2003 | Maughan et al. | |
| 2003/0126148 A1 | 7/2003 | Gropper et al. | |

(Continued)

FOREIGN PATENT DOCUMENTS

JP 2002312373 A 10/2002

(Continued)

OTHER PUBLICATIONS

U.S. Appl. No. 11/678,997, filed Feb. 26, 2007, Friedlander et al.

(Continued)

*Primary Examiner* — Sheetal R Rangrej
(74) *Attorney, Agent, or Firm* — Yee & Associates, P.C.; John R. Pivnichny

(57) ABSTRACT

A computer implemented method for generating optimized pharmaceutical treatment plans for an individual. A set of known treatments to be used by the target individual over a future period of time is generated. An actual use of the treatments in the set of known treatments by the target individual during the future period of time is substantially certain. A set of probable treatments of the target individual is received. The actual use of the treatments in the set of probable treatments by the target individual during the future period of time is uncertain. An optimized pharmaceutical treatment plan for the target individual is generated. The optimized pharmaceutical treatment plan comprises medications and durable medical goods that are likely to be used by the target individual over the future period of time optimized over a set of dimensions associated with the set of known treatments and the set of probable treatments.

25 Claims, 7 Drawing Sheets

U.S. PATENT DOCUMENTS

| | | |
|---|---|---|
| 2003/0177132 A1 | 9/2003 | Thomas et al. |
| 2003/0191699 A1 | 10/2003 | Deveault et al. |
| 2003/0195898 A1 | 10/2003 | Agarwal et al. |
| 2004/0122719 A1* | 6/2004 | Sabol et al. ............... 705/7 |
| 2005/0149466 A1 | 7/2005 | Hale et al. |
| 2006/0004609 A1* | 1/2006 | Kenneth et al. ............ 705/3 |
| 2006/0149705 A1 | 7/2006 | Friedlander et al. |
| 2007/0027636 A1* | 2/2007 | Rabinowitz ............... 702/20 |
| 2007/0276851 A1 | 11/2007 | Friedlander et al. |
| 2008/0082356 A1 | 4/2008 | Friedlander et al. |

FOREIGN PATENT DOCUMENTS

| | | |
|---|---|---|
| JP | 2002342484 A | 11/2002 |
| WO | WO 0100807 A1 | 1/2001 |

OTHER PUBLICATIONS

U.S. Appl. No. 11/678,957, filed Feb. 26, 2007, Friedlander et al.

Shelfer et al., "Smart Card Evolution", Communications of the ACM, Jul. 2002, pp. 83-88, vol. 45 No. 7, ACM.

Grimson et al., "The SI Challenge in Health Care", Communications of the ACM, Jun. 2000, pp. 49-55, ACM.

Lowery et al., "Barriers to Implementing Simulation in Health Care", Proceedings from the 1994 Winter Simulation Conference, pp. 868-875.

Goodwin et al., "Data Mining for Preterm Birth Prediction", 2000, pp. 46-51, ACM.

* cited by examiner

OPTIMIZING PHARMACEUTICAL TREATMENT PLANS ACROSS MULTIPLE DIMENSIONS

BACKGROUND OF THE INVENTION

1. Field of the Invention

The present invention relates generally to an improved data processing system, and more specifically to optimizing treatment plans. More particularly, the present invention relates to a computer implemented method, apparatus, and computer usable program product for optimizing pharmaceutical treatment plans across multiple optimized dimensions and accommodating complex uncertainty.

2. Background Description

A pharmaceutical treatment plan is a plan that includes the prescription drugs, non-prescription drugs, and/or durable medical devices required by an individual. The pharmaceutical treatment plan may specify dosages of drugs, brand names of drugs and medical goods manufacturers, as well as other treatment details. As the field of healthcare continues to advance and become more specialized, the variety of pharmaceutical treatment options, available drugs, types of drugs, medical specialists, treatment location choices, and health care insurance plan options also continues to increase. In addition, the amount of medical information associated with an individual and the individual's medical options has also grown.

However, the medical information associated with an individual, the individual's treatment needs, treatment options, treatment providers, and various treatment plans are stored at various locations by various health care providers, organizations, and/or individuals. Thus, it may be difficult and time consuming for an individual to access all the information necessary to generate pharmaceutical treatment plans. Moreover, pharmaceutical treatment plans are typically sub-optimal because individuals and healthcare practitioners often lack the skills, time, knowledge, and/or expertise needed to optimize treatment plans across multiple dimensions.

BRIEF SUMMARY OF THE INVENTION

According to one embodiment of the present invention, a computer implemented method is provided for generating optimized pharmaceutical treatment plans for an individual. Medical data associated with a target individual is analyzed. A set of known treatments to be used by the target individual over a future period of time is generated. The set of known treatments comprises medications and durable medical goods known to be needed by the target individual over the future period of time. An actual use of the treatments in the set of known treatments by the target individual during the future period of time is substantially certain. In response to sending a query to an inference engine requesting inferences associated with possible treatments that are likely to be needed by the target individual, a set of probable treatments of the target individual is received. The set of probable treatments comprises medications and durable medical goods that are likely to be needed by the target individual during the future period of time. The actual use of the treatments in the set of probable treatments by the target individual during the future period of time is uncertain. An optimized pharmaceutical treatment plan for the target individual is generated. The optimized pharmaceutical treatment plan comprises medications and durable medical goods that are likely to be used by the target individual over the future period of time. The optimized pharmaceutical treatment plan is optimized over a set of dimensions associated with the set of known treatments and the set of probable treatments.

DETAILED DESCRIPTION OF THE INVENTION

Figure 1:
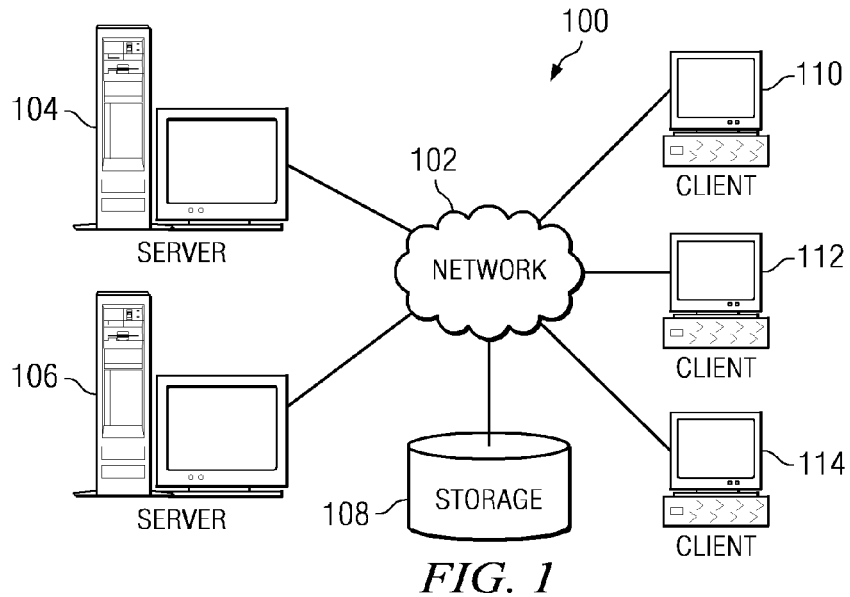
FIG. 1 is a block diagram of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disc, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
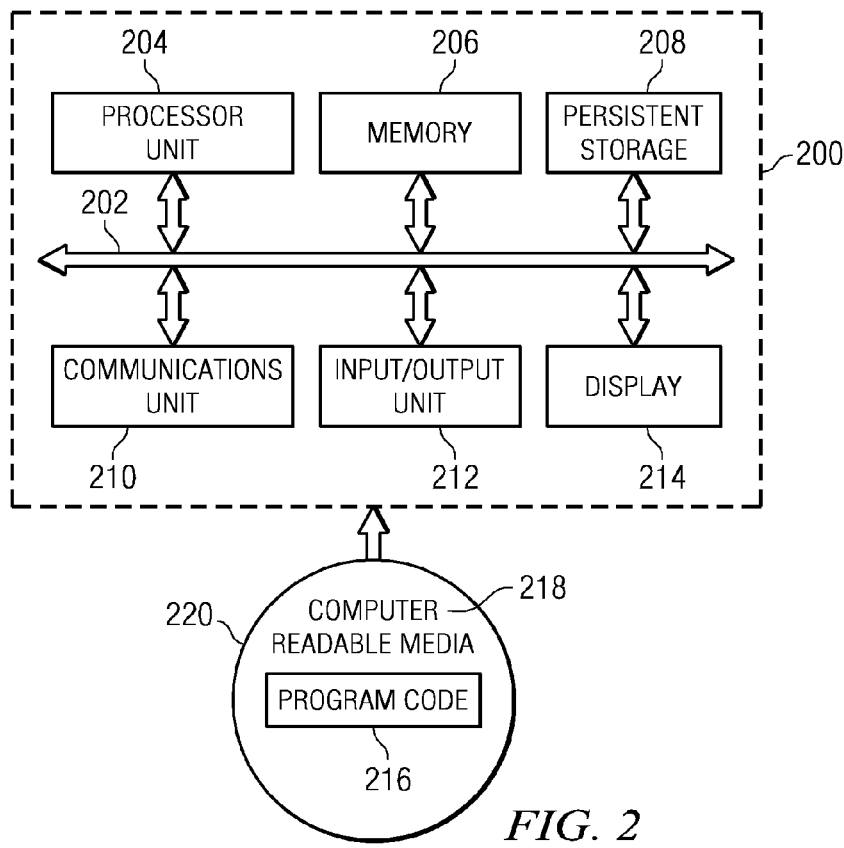
FIG. 2 is a block diagram of a data processing system in which illustrative embodiments may be implemented.

With reference now to the figures, and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disc, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

The different components illustrated for data processing system 200 are not meant to provide architectural limitations to the manner in which different embodiments may be implemented. The different illustrative embodiments may be implemented in a data processing system including components in addition to, or in place of, those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments recognize that individual patients have a need to predict the medical treatments and pharmaceuticals that the individual may need in the future, such as in the next year. An individual may need this information to assist in selecting a health insurance plan, budgeting costs for medical care in the next year, and selecting physicians and treatment centers. Some medications and treatments can be predicted with some certainty. For example, if an individual has type 1 diabetes, the individual can predict that insulin, needles, and blood sugar testing equipment will be needed with some certainty. In addition, it can be predicted that children will require certain vaccinations at certain stages in their lives.

However, the embodiments recognize that some medical needs are less certain. For example, it is far less certain as to whether a child will have an ear infection and require antibiotics or other treatments. The embodiments recognize a need for an individual to be able to determine known and probabilistic medical treatment requirements, particularly with regard to pharmaceuticals and durable medical goods, to determine an expected consumption of medical drugs as well as durable medical goods and/or compare the expected consumption of medical treatments to various plans offered by health insurance companies.

According to one embodiment of the present invention, a computer implemented method is provided for generating optimized pharmaceutical treatment plans for an individual. A pharmaceutical treatment plan includes, without limitation, prescription drugs, non-prescription (over-the-counter) drugs, durable medical devices, and other treatments. Treatments are processes, medical procedures, drugs, actions, lifestyle changes, or other treatments prescribed for a specified purpose.

Medical data associated with a target individual is analyzed. A set of known treatments to be used by the target individual over a future period of time is generated. As used herein, the term set refers to one or more. The set of known treatments comprises medications and durable medical goods known to be needed by the target individual over the future period of time. An actual use of the treatments in the set of known treatments by the target individual during the future period of time is substantially certain. A query is sent to an inference engine requesting inferences associated with possible treatments that are likely to be needed by the target individual.

A set of probable treatments of the target individual is received. The set of probable treatments comprises medications and durable medical goods that are likely to be needed by the target individual during the future period of time. The actual use of the treatments in the set of probable treatments by the target individual during the future period of time is uncertain.

An optimized pharmaceutical treatment plan for the target individual is generated. It will be appreciated by one skilled in the art that the words "optimize", "optimization" and related terms are terms of art that refer to improvements in selecting and/or generating treatment plans, and do not purport to indicate that a computer program has achieved, or is capable of achieving, an "optimal" or perfect treatment plan.

The optimized pharmaceutical treatment plan comprises medications and durable medical goods that are likely to be used by the target individual over a future period of time. The optimized pharmaceutical treatment plan is optimized over a set of dimensions associated with the set of known treatments and the set of probable treatments. The pharmaceutical treatment plan may optionally include treatment facility locations where the target individual goes to receive a treatment. The pharmaceutical treatment plan may optionally include one or more health insurance plan options that would provide the best health insurance coverage in light of the known and probable pharmaceutical treatment needs of the target patient.

Figure 3:
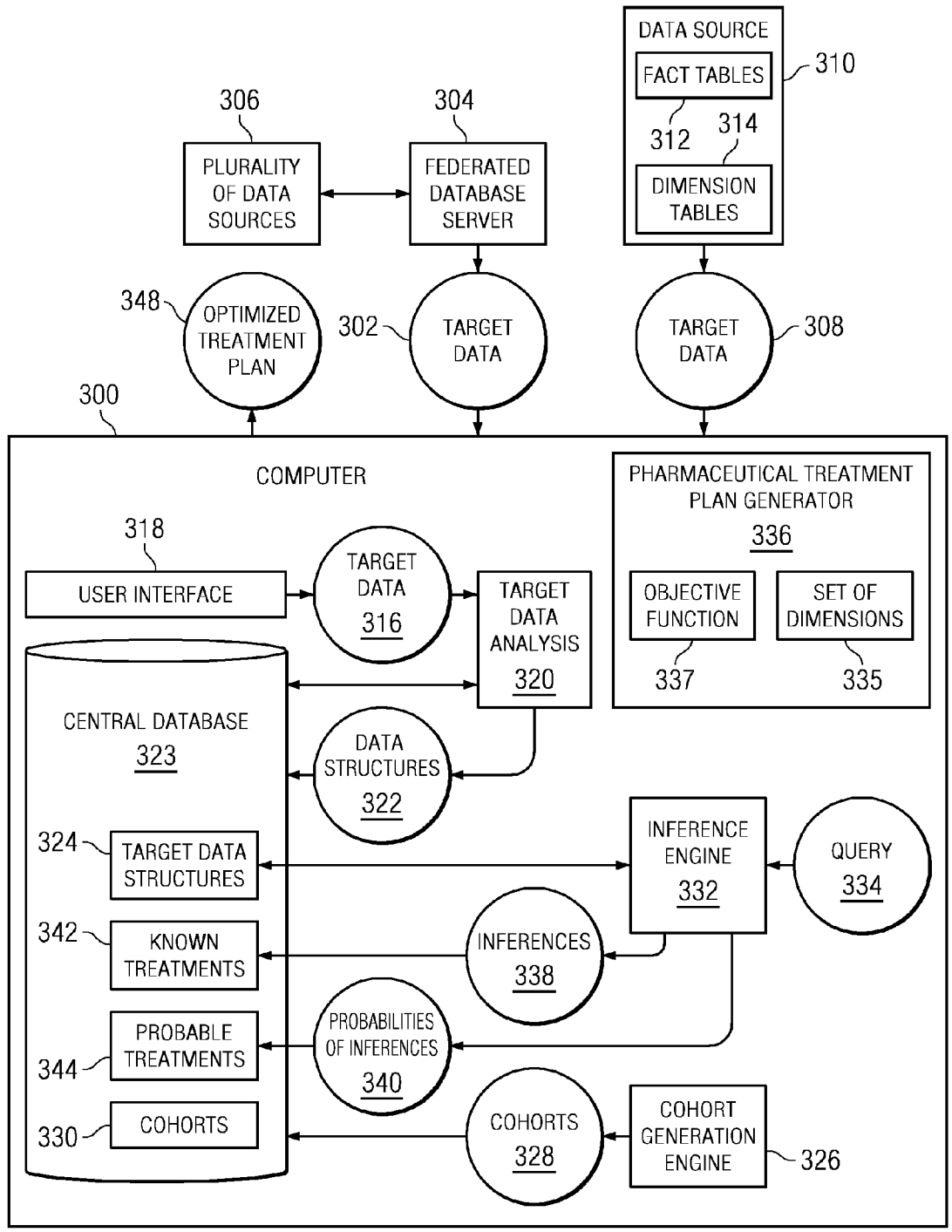
FIG. 3 is a block diagram of a pharmaceutical treatment plan optimization system in accordance with an illustrative embodiment.

FIG. 3 is a block diagram of a pharmaceutical treatment plan optimization system in accordance with an illustrative embodiment. Computer 300 may be implemented using any type of computing device, such as a server, a client computer, a laptop computer, a personal digital assistant (PDA), or any other computing device depicted in FIGS. 1 and 2.

Computer 300 receives target data 302 from federated database server 304. Federated database server 304 is associated with plurality of data sources 306. Plurality of data sources 306 comprises two or more data sources having medical data. Medical data is information describing the health and/or medical history of a target individual, information describing one or more physicians, one or more health care insurance plans and the plan's medical coverage, medications, side effects of the medications, and/or one or more medical care treatment facilities. A medical care treatment facility is a facility for treating patients, such as a hospital, a clinic, a doctor's office, a minor emergency care center, a nurse's station, or any other medical treatment center. The data sources may be remote to federated database server 304 and/or local to federated database server 304. In other words, the data sources in plurality of data sources 306 may be distributed across many different computing devices and/or machines.

In addition, computer 300 is not required to receive medical data from a single federated database server 304. Computer 300 may receive no medical data from a federated database server, receive medical data from a single federated database server, or receive medical data from a set of two or more federated database servers.

In this example, computer 300 optionally receives target data 308 from data source 310. Data source 310 is a source of medical data. Data source 310 comprises fact tables 312 and dimension tables 314. Fact tables 312 are two or more tables that include or store a value corresponding to an observed value. For example, the fact table may include a test result, a patient's blood sugar, a medication dosage, a known side effect of a prescribed medication, a location of a treatment center, a distance of the treatment center from the target individual's home, a brand name of a drug covered by a particular health insurance plan, or any other fact. The fact tables also include one or more identification keys. The identification keys may be a symbol, a series of number or letters, or any combination thereof. The identification keys identify dimension tables 314.

A dimension table provides additional information about the fact stored in a fact table associated with the dimension table. For example, a dimension table accessed using the associated identification key stored in the fact table may include information about the test performed that provided the result stored in the fact table, information about the patient, information about the provider, information about the person who requested the test or authorized the test, the date and/or time of the test, international standards and the like. The dimension tables may allow drilling in and out of the data stored in the dimension tables. For example, if the dimension table associated with the date is accessed using the associated identification key, the date of the test may be drilled out to the week of the test, the month of the test, the year of the test, and so forth.

Data source 310 may be a single data source, such as a database. Data source 310 may also comprise a plurality of two or more data sources. The data sources may be located on a single computing device or on a plurality of different computing devices. Computer 300 also optionally receives target data 316 manually entered by a user through user interface 318. User interface 318 is any type of known or available interface for providing input to computer 300, including but not limited to, a graphical user interface (GUI), a menu-driven interface, a command line interface, a touch screen, a voice recognition system, an alphanumeric keyboard, a mouse, any other interface for entering input, and/or any combination of interfaces.

Target data 302, target data 308, and target data 316 is medical data and other data associated with the target individual. Target data 302, target data 308, and target data 316 may also include medical information associated with one or more cohorts of the target individual. For example, and without limitation, the target data may include patient data, demographic data, family health history data, genetic data, phenotypic data, current and past vital signs, laboratory test results, current and previous prescriptions/drug treatment history, allergies, antibiotic resistant infections, side-effects and complications of current and past treatments and medications, admissions-discharge-treatment records, current and previous treating physicians, locations of medical treatment facilities utilized by the target individual, locations of all treatment facilities within a given radius of the target individual's residence or workplace, location of all treatment facilities specializing in treatment of any illness associated with the target individual, gender, age, current and past illnesses, history of drug abuse, surgeries, occupation and/or occupational health hazards, and/or any other data associated with the target individual's past, present, or future medical care, available treatment facilities, healthcare professionals, and/or available medical treatments.

In this example, computer 300 receives the medical data from federated database server 304, data source 310, and from a user associated with user interface 318. However, the embodiments are not limited to receiving medical data from only these sources. Computer 300 may also receive medical data from a local data source, data retrieved off the internet by a web crawler, data miner, or other data extraction software component, or any other source. Computer 300 also determines whether data should be federated or accessed via extract, transform, and load (ETL) techniques. Federated access to data is made by accessing desired data piecemeal. Extract, transform, and load techniques allow access to data by extracting, transforming, and loading all data onto a local network or data processing system. The decision of whether data should be made available via federation or extract, transform, and load techniques can be important.

Target data analysis 320 is a software component for identifying medical data of interest to pharmaceutical treatment plan generator 336 for use in generating optimizing treatment plans. Target data analysis 320 may optionally use data mining functionality on target data 302, 308, and 316 and/or on data in any other interconnected databases. In one example, target data analysis 320 comprises a data mining program, such as DB2 Intelligent Miner produced by International Business Machines Corporation. Data mining is the process of automatically searching large volumes of data for patterns. Data mining may be further defined as the nontrivial extraction of implicit, previously unknown, and potentially useful information from data. Data mining application uses computational techniques from statistics, information theory, machine learning, and pattern recognition.

Target data analysis 320 selects data, analyzes data, shows data patterns, sorts data, and determines relationships between data. Target data analysis 320 generates data structures 322. Data structures 322 are structures for storing data so that it can be used efficiently by computer 300 in FIG. 3. Data structures 322 may include any type of data structures, including, without limitation, binary tree (B tree) type of branching linked data structure, routing tables, or any other type of data structure. Data structures 322 may include arrays, records, unions, and/or references. Data structures 322 are stored in central database 323 as target data structures 324 for utilization by pharmaceutical treatment plan generator 336, inference engine 332, and/or cohort generation engine 326.

Cohort generation engine 326 is a software component for automatically generating cohorts 328. A cohort is a group of individuals, machines, components, or modules identified by a set of one or more common characteristics. Cohorts 328 are used to identify the effectiveness, side effects, complications, and/or quality of life for patients taking various pharmaceuticals, receiving particular treatments, and utilizing various durable medical goods.

For example, if a target individual has sleep apnea, cohorts 328 may show that a cohort group having sleep apnea typically suffers from respiratory ailments. These respiratory ailments can be identified as probable side effects of the sleep apnea condition. Probable treatments typically used to treat the respirator ailments may then be identified as probable treatments that will be needed by the target individual. Likewise, cohorts 328 may show that cohort groups having the same occupation as the individual, are prone to respirator ailments.

Cohorts 328 may be used to determine the success rate of a particular drug or other treatment in individuals in the same cohort as the target individual. Cohorts 328 may be used to determine the side effects, secondary infections, and hospital acquired infection rates in individuals in a cohort receiving pharmaceuticals, surgery, utilizing durable medical devices, and/or receiving other treatments from a particular physician, in a particular treatment facility, and/or at a particular dosage or frequency level.

This information is used to optimize a pharmaceutical treatment plan for the target individual that is optimized across set of dimensions 335. Cohorts 328 that are of interest to pharmaceutical treatment plan generator 336 for optimizing a pharmaceutical treatment plan for the target individual are stored in central database 323 as cohorts 330.

Inference engine 332 is a software component for generating inferences 338 and probabilities of inferences 340. Pharmaceutical treatment plan generator 336 is able to determine the known treatments that will be required by the target individual. However, pharmaceutical treatment plan generator 336 is unable to determine other treatments that are likely to be used by the target individual but not certain to be used or needed. Therefore, pharmaceutical treatment generator 336 sends query 334 to inference engine 332. Query 334 is a request for probable medications and/or treatments that may be required by a target individual.

In response to receiving query 334, inference engine 332 generates inferences 338 and probabilities of inferences 340. Inferences 338 are conclusions based on a comparison of facts within central database 323. Probabilities of inferences 340 are probabilities of the likelihood that a particular inference is true, or alternatively, the probability that the particular inference is false.

Inferences 338 and probabilities of inferences 340 are used by pharmaceutical treatment plan generator 336 to identify one or more probable treatments that may be required by the target individual. These identified probable treatments are stored as probable treatments 344 in central database 323.

Pharmaceutical and treatment plan generator 336 is a software component for generating optimized pharmaceutical treatment plans optimized over set of dimensions 335. Set of dimensions 335 is a set of one or more dimensions associated with a pharmaceutical treatment plan. Pharmaceutical treatment plan generator 336 generates a treatment plan that is optimized across one or more dimensions. The dimensions may include, without limitation, cost, quality of life, side effects/complications, medical insurance plan coverage, success rate, and/or any other dimensions.

Set of dimensions 335 includes two or more dimensions selected by a user. In another embodiment, set of dimensions may include one or more dimensions that are pre-set or predetermined. For example, set of dimensions 335 may be preset to select treatments that will maximize the quality of life or the success rate of treatment. Other dimensions, such as costs and location of treatment centers may be selected by the user.

Pharmaceutical treatment plan 336 generates object function 337. Object function 337 is mathematical programming or optimization component that seeks to minimize or maximize a real function by systematically choosing the values from within an allowed set. Object function 337 is optimized for a particular target individual. In this case, object function 337 seeks to maximize or minimize one or more dimensions in set of dimensions 335. For example, if the selected dimensions are cost and quality of life, object function 337 selects available pharmaceuticals, such as prescription and non-prescription drugs, that minimize costs to the target individual and result in the best or maximum quality of life. Thus, if three types of medication are available to treat a condition of the target individual, objective function 337 selects the brand of medication that is less expensive and most likely to result in the fewest negative side effects to the target individual based on the dosage of the medication, the other drugs and treatments being taken by the target individual, the target individual's age, and other data associated with the target individual to minimize costs and maximize quality of life.

If a user selects a new set of dimensions, pharmaceutical treatment plan generator 336 optimizes the treatment plan to generate a new optimized pharmaceutical treatment plan that is optimized over the new set of dimensions. For example, if a user selects a first set of dimensions that includes minimizing costs and travel, a first pharmaceutical treatment plan is generated. If the user then selects a new set of dimensions that includes success of treatment and quality of life instead of costs and travel, a different pharmaceutical treatment plan is generated that may include a different set of prescription and non-prescription drugs, as well as other different treatments.

Known treatments 342 include medications and durable medical goods known to be needed by the target individual over a future period of time. It is substantially certain that the target individual will actually use the treatments in the set of known treatments during the future period of time. For example, if the target individual has type 2 diabetes, it is substantially certain that the target individual will continue to need insulin pills and regular blood sugar testing during any time in the future. Likewise, if the target individual is a child, known treatments may include regularly scheduled vaccinations.

Probable treatments 344 include medications and durable medical goods that are likely to be needed by the target individual during a future period of time. It is uncertain as to whether the target individual will actually need and/or use the treatments in the set of probable treatments during the future period of time. For example, if the target individual is a child that is susceptible to contracting strep throat (streptococcus), probable treatments 344 for the child may include a sufficient amount of antibiotics to treat one or more incidents of strep throat during the future time period. However, it is not certain that the child will contract strep throat in the future. The child may in fact never contract strep throat in the future, even though it appears to be statistically likely that the child will have strep throat again. Thus, the treatment for future occurrences of strep throat in the child will always be probable, but not definite or certain, until the future point in time at which the child actually becomes ill with strep throat. In contrast, if the child has diabetes, it is substantially certain that the child will require insulin in the future. Thus, insulin for treating diabetes is always a known treatment.

The set of probable treatments may include the inferences and the probabilities of those inferences occurring. In another embodiment, the set of probable treatments includes only those treatments in the inferences with a probability of the inferences that is greater than a threshold probability. For example, a threshold probability may be fifty-one percent or greater.

Optimized treatment plan 348 is a pharmaceutical treatment plan that is optimized across multiple dimensions weighted to the specific needs of the target individual. Optimization treatment plan 348 may include, without limitation, medications and/or durable medical goods that are likely to be used by the target individual over a given time period in the future. Optimized treatment plan 348 is substantially the best pharmaceutical treatment plan in a plurality of possible pharmaceutical treatment plans in light of the selected dimensions in set of dimensions. In other words, many possible combinations and types of medicines and durable medical devices may be possible, but optimized treatment plan 348 is the treatment plan that optimizes the selected dimensions better than the other possible pharmaceutical plans.

Figure 4:
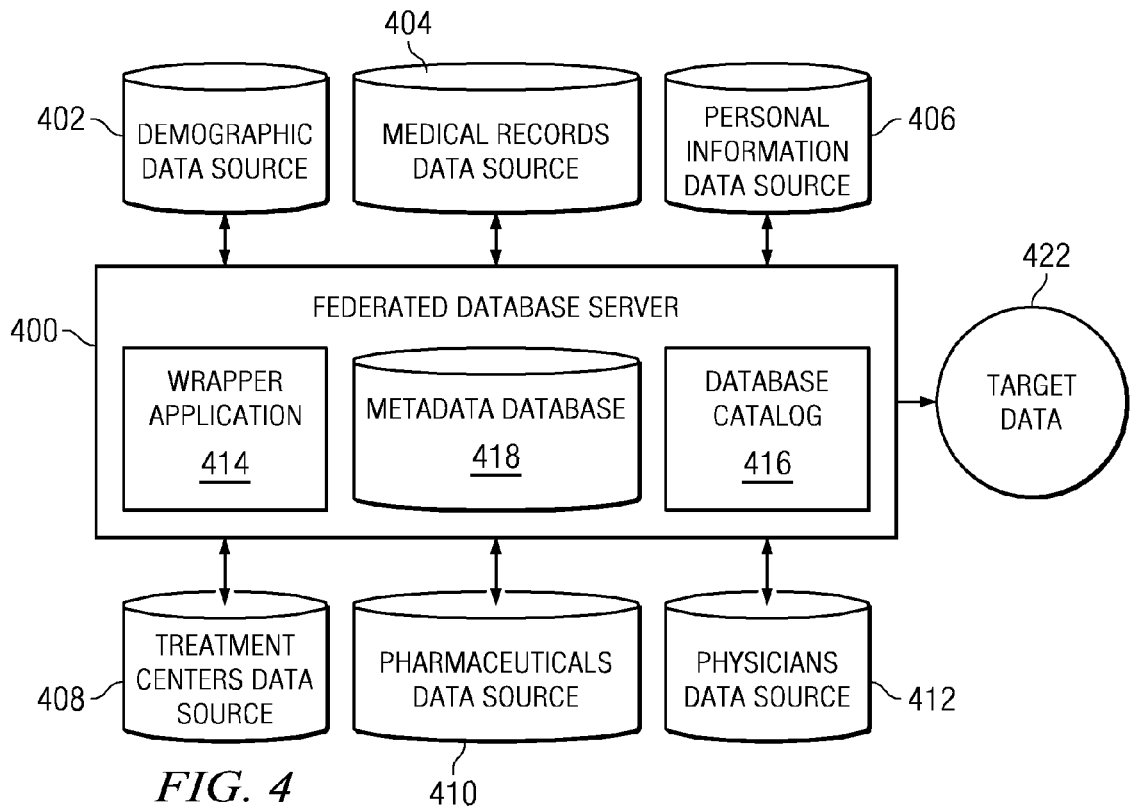
FIG. 4 is a block diagram of a federated database server in accordance with an illustrative embodiment.

FIG. 4 is a block diagram of a federated database server in accordance with an illustrative embodiment. Federated database server 400 is a server associated with a federated database, such as federated database server 304 in FIG. 3.

Federated database server 400 is a meta-database management system which transparently integrates multiple autonomous database systems into a single virtual database, that is, a federated database. The constituent database systems remain autonomous, separate, and distinct. In this example, the constituent database systems include a plurality of data sources, such as, without limitation, demographic data source 402, medical records data source 404, personal information data source 406, treatment centers data source 408, pharmaceutical data source 410, and physicians data source 412.

Demographic data source 402 comprises one or more sources of data providing demographic information associated with the target individual and/or other individuals that have received or are receiving medical treatments. Medical records data source 404 comprises one or more sources of medical records for the target individual and/or other individuals receiving medical treatments.

Personal information data source 406 is one or more sources of personal information regarding the target individual and/or other individuals that are, or have received, medical treatments. Treatment centers data sources 408 is one or more sources of data describing medical treatment facilities, such as, without limitation, hospitals, non-emergency clinics, doctor offices, nurses stations, red cross stations, diagnostic centers, outpatient care facilities, nursing homes, and/or assisted living, and/or any other facility providing medical care.

Pharmaceutical data source 410 is one or more sources of information regarding prescription drugs, non-prescription drugs, vaccinations, and/or durable medical devices. Physician data source 412 includes one or more sources of data describing physicians, hospital affiliations/privileges of the physicians, specialists, locations of offices, physicians specializing in providing particular treatments, physicians on particular health care insurance plans, and/or any other information regarding physicians.

The data sources shown in FIG. 4 are only examples of possible data sources associated with federated database server 400. Federated database server 400 is not required to have access to all of the types of data sources depicted in FIG. 4. Moreover, federated database server 400 may have access to additional data sources not shown in FIG. 4. For example, federated database server 400 may have access to health insurance plan options data sources that provide information regarding various health insurance plans, the cost of each plan, the drugs and procedures covered by each plan, the physicians affiliated with each plan, the treatment centers covered by each plan, and any other information regarding available health insurance plan options and coverage.

Wrapper application 414 is software for generating wrappers. Wrappers are software modules that enable federated database server 400 to communicate with the data sources. A wrapper is generated for each data source or each type of data source.

Database catalog 416 is a directory or index for tracking the data sources locations, types of data, wrapper associated with each data source, and any other information regarding a data source. Metadata database 418 is a database for storing data describing each data source.

An application, such as a pharmaceutical treatment plan generator, can submit a query to federated database server 400. In response, federated database server 400 optimizes the query, develops an execution plan that decomposes the query into a plurality of queries that can be executed at each data source, and invokes the appropriate wrappers to execute the queries to the data sources. The data returned to federated database server 400 from the data sources in response to the query are combined and processed by federated database server 400 to form target data 422. Target data 422 is data associated with target individual and/or medical treatments, such as target data 302 in FIG. 3.

Figure 5:
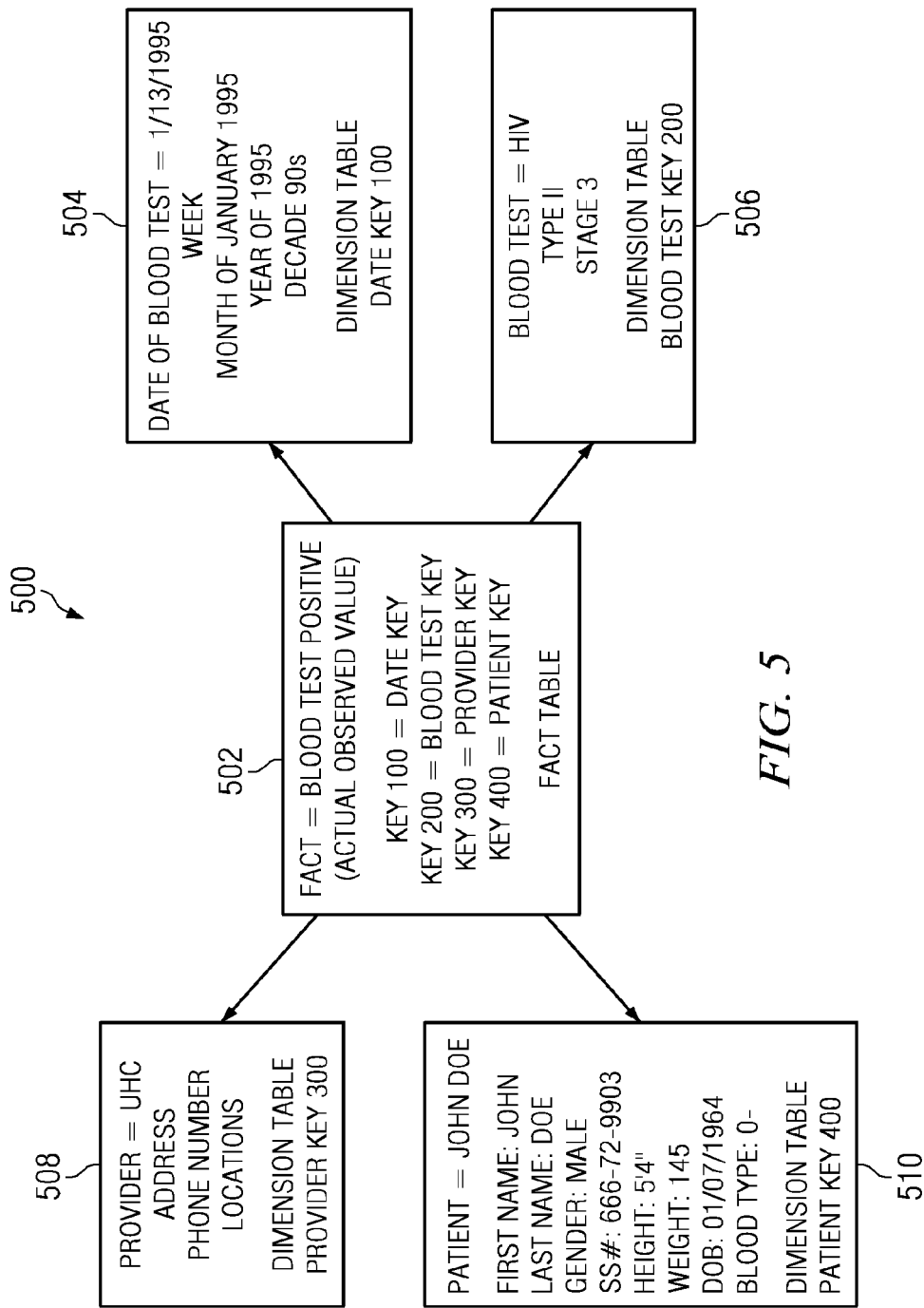
FIG. 5 is a block diagram of a data source having a fact table and dimension tables in accordance with an illustrative embodiment.

FIG. 5 is a block diagram of a data source having a fact table and dimension tables in accordance with an illustrative embodiment. Data source 500 is a data source having fact tables and dimension tables, such as data source 310 in FIG. 3.

Fact table 502 includes an observation that this patient's blood tested positive for diabetes and identification keys 504-510, which identify different dimension tables associated with fact table 500.

It will be understood that FIG. 5 is only an exemplary embodiment of fact tables and dimension tables according to some embodiments of the present invention and, therefore, embodiments of the present invention should not be limited to the configuration illustrated therein. For example, more or less than four dimension tables may be provided without departing from the teachings of the present invention.

Dimension table 502 associated with date key 100 provides information about the date of the blood test in fact table 500 was taken. The information provided in the date dimension table may also be drilled out to the week, month or year in which the test was taken.

The blood test key 200 provides access to blood test dimension table 506. Blood test dimension table 506 may provide information about the blood test, for example, the positive blood test was for type II diabetes in stage 3. This information may be drilled out beyond the blood test level to all blood tests for this patient, all blood tests for any patients having similar results and the like.

The provider key 300 provides access to provider dimension table 508. Provider dimension table 508 may provide information about the patient's healthcare provider, for example, United Healthcare (UHC). Dimension table 508 may include the provider's address, telephone number, copay, locations and the like.

Finally, the patient key 400 provides access to patient dimension table 510, which provides information about the patient having the positive blood test. Patient dimension table 510 may include the patient's first and last name, gender, social security number, height, weight, date of birth, blood type and the like.

The dimension tables according to some embodiments of the present invention may be expanded to provide a broader view of the information available in the database or a narrower view of the information provided in the database (drill in and out). For example, the criteria of interest may be side effects and/or adverse reactions to a particular brand of drug and/or dosage of the drug. The results of this query may be quite large as the side effects and adverse reactions may range from a rash to death. Thus, the information may be narrowed to just those patients who experienced a rash as a result of taking the drug. The information may be further narrowed to look at each patient experiencing the rash individually or patients that are women between the ages of 20 and 40. Furthermore, the type of drug may be expanded to provide all of the drugs in the particular class of drugs. These examples of drilling in and out of the data are provided for exemplary purposes only and, therefore, embodiments of the present invention are not be limited to these examples.

A first set of data, by itself, may be of little value, but together with other data combinations of the first set of data and other data, patterns associated with the quality of life of patients receiving certain drugs at particular dosages, rates of hospital acquired infections, treatment complications, and costs of treatments, may become evident. Similarly, patterns or events are often discernable only by piecing together data from multiple individuals or cohorts spread throughout the data. Cohorts are groups of objects or people that share common characteristics or are otherwise part of a group.

Figure 6:
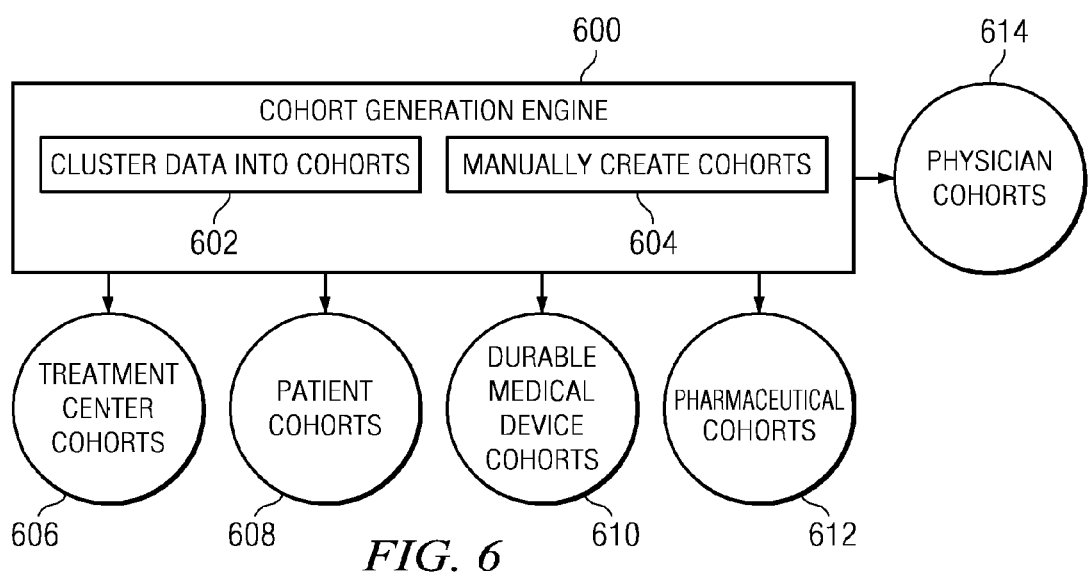
FIG. 6 is a block diagram illustrating a cohort generation engine in accordance with an illustrative embodiment.

Referring now to FIG. 6, a block diagram illustrating a cohort generation engine is depicted in accordance with an illustrative embodiment. Cohort generation engine 600 is a software component for generating cohorts, such as cohort generation engine 326.

Cluster data into cohorts 602 is a software component of cohort generation engine 600 for clustering target data into cohorts. Cohort generation engine 600 automatically generates cohorts and sub-cohorts using data stored at an atomic level in the central database storing information associated with the target individual. Atomic data is data stored at the finest possible degree of granularity. Thus, this process of generating cohorts is powerful in that cohorts can be generated involving any given individual type of data. For example, individuals need not be associated into a cohort in order to associate prescribed medications into a cohort. A group of prescribed medications can be generated into a cohort according to any parameter, such as, for example, dosage, date of prescription, illness being treated, occupation of recipient, cost of prescription, equivalent brands of the prescription medication, or any other parameter. A group of individuals receiving the medication can be in one cohort, a group of equivalent generic brand medications in another cohort, and a group of individuals experiencing side effects from the medication can be a third cohort. A fourth cohort can be automatically generated that represents all individuals in the first cohort having successfully completed the course of treatment involving the equivalent generic brand of the medication without suffering significant negative side effects. This information can be important for optimizing pharmaceutical treatment plans by cost, side effects/complications, quality of life, success rate of treatment, or any other dimensions.

Cohort generation engine 600 optionally includes manually create cohort 604 component for receiving manually created cohorts. Manually create cohort 604 allows one or more users to manually create a cohort. A cohort can be manually created by inputting a command to the central database or other software or hardware. The command can be to associate one set of data with another set of data. For example, a user can input a command to associate "age 49" with "side effects of nitroglycerine" to create a cohort of "49 year old patients suffering side effects from nitroglycerine." Central database 323 in FIG. 3 allows this command to be executed successfully. The cohorts themselves, however, are generated and stored as data in the central database.

In this example, the cohorts include, but are not limited to, treatment center cohorts 606, patient cohorts, durable medical device cohorts 610, pharmaceutical cohorts, and/or physician cohort 614. Treatment center cohort 606 is a cohort group comprising treatment centers. Likewise, patient cohorts 608 is a cohort group having patients as members of the cohort. Thus, each generated cohort becomes a new datum for use in central database 323 in FIG. 3.

Figure 7:
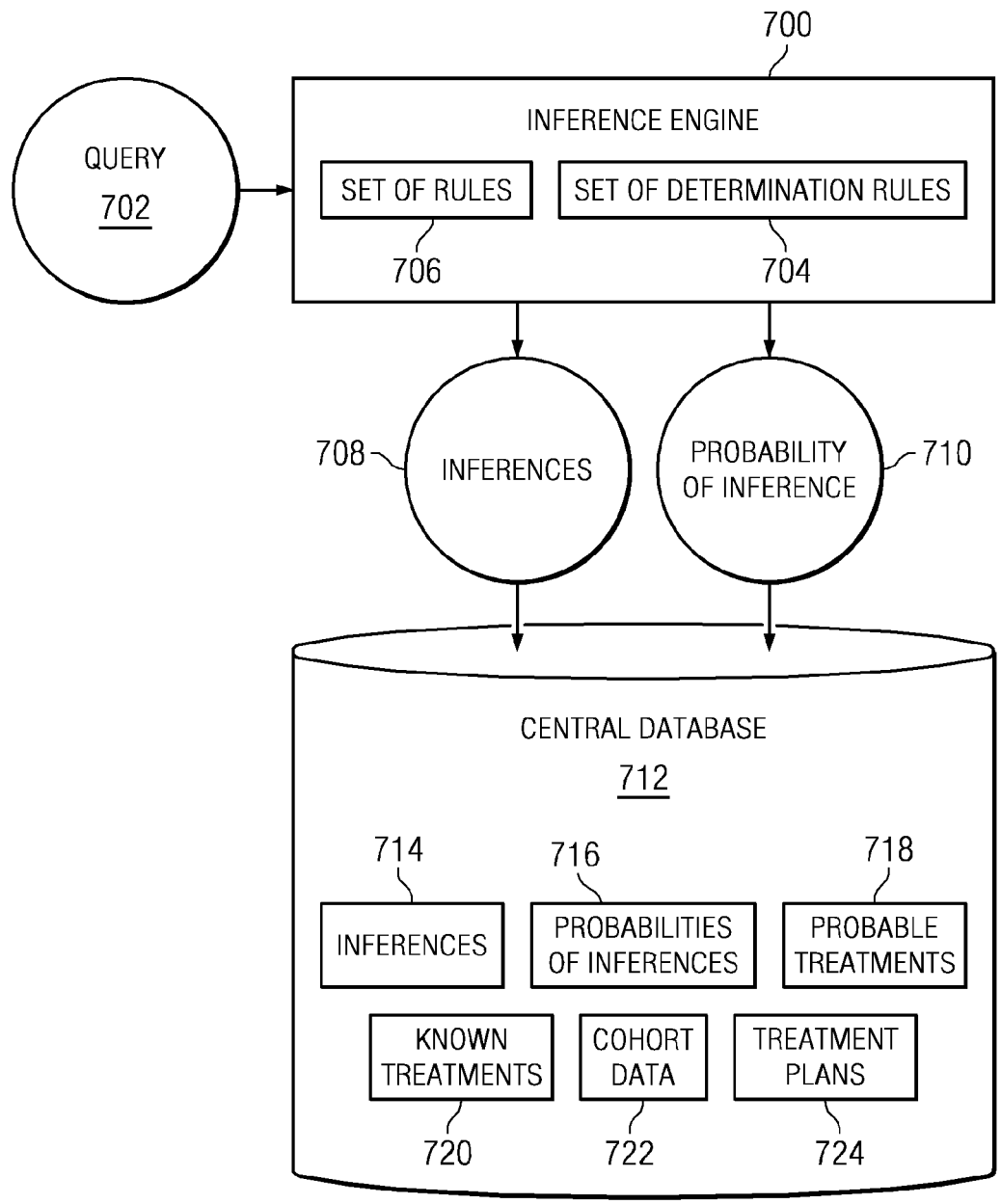
FIG. 7 is a block diagram illustrating an inference engine in accordance with an illustrative embodiment.

FIG. 7 is a block diagram illustrating an inference engine in accordance with an illustrative embodiment. Inference engine 700 is a software component for generating inferences and probabilities of inferences using medical data associated with a target individual, such as inference engine 332 in FIG. 3.

Query 702 is a request for a fact, such as probable medications and/or treatments that may be required by a target individual. Query 702 may be a single query or a set of two or more queries. In response to receiving query 702, inference engine 700 uses query 702 as a frame of reference to find relevant information in central database 712 based on query 702. A frame of reference is an anchor datum or set of data that is used to limit which data are searched in central database 712. The frame of reference is used to establish set of determination rules 704.

Set of determination rules 704 is a set of rules that are used to generate set of rules 706. Set of rules 706 specifies information to be searched. For example, if query 702 requests probable antibiotics that may be needed, set of rules 706 may specify searching for past history of infections in the target individual that required antibiotics. Set of determination rules 704 may also specify certain interrelationships between data sets that will be searched. Inference engine 700 uses data in centralized database 712 to derive inference 708 and probability of inference 710 based on comparison of data within centralized database 712 according to set of rules 706. Inference engine 700 does not compare the entirety of the data in central database 712 with every possible combination in order that limited computing resources can execute desired queries.

Central database 712 is a database for storing target data associated with a target individual, such as, without limitation, central database 323 in FIG. 3. Central database 712 stores any data associated with the target individual and/or other data relating to medical treatments, pharmaceuticals, physicians, treatment facilities, and/or other medical data. For example, and without limitation, the data stored in central database 712 may include cohort data 722, inferences 714, probabilities of inferences 716, probable treatments 718, known treatments 718, and/or treatment plans 724.

Inferences 714 are inferences generated by inference engine 700. Inferences 714 include inferences regarding possible pharmaceuticals and/or durable medical goods that may be required by the target individual in the future. The inferences may be true or false. A probability of inferences 716 indicates the likelihood or percentage chance that each inference in inferences 714 is true or false.

Probable treatments 718 is a set of one or more pharmaceuticals and/or durable medical goods that may be needed or used by the target individual during some future time period. Probable treatments 718 are treatments that are likely to be needed. However, it is uncertain as to whether the target individual will actually use or need the pharmaceuticals and/or durable medical goods during the future time period.

Known treatments 720 is a set of one or more pharmaceuticals, durable medical goods, or other treatments that the target individual will use or require during a given future time period. The treatments in known treatments 720 can be identified as treatments that will be needed by the target individual with a degree of certainty. For example, if the target individual has a heart condition and a doctor has prescribed that the patient take an aspirin every day, it is reasonably certain the target individual will need an aspirin every day during the future time period. Thus, if the future time period encompasses one year, known treatments 720 will include 365 aspirin tablets.

Cohort data 722 is data describing one or more cohorts generated by a cohort generation engine, such as cohort generation engine 326 in FIG. 3. Treatment plans 724 is a set of two or more treatment plans that can be optimized across one or more dimensions. In this example, a pharmaceutical treatment plan generator component can modify one or more treatment plans in treatment plans 724 to generate an optimized pharmaceutical treatment plan. In another example, treatment plans 724 includes templates for treatment plans. Pharmaceutical treatment plan generator uses the optimized pharmaceuticals, durable medical goods, and/or other treatments in conjunction with one or more templates in treatment plans 724 to generate an optimized treatment plan.

Figure 8:
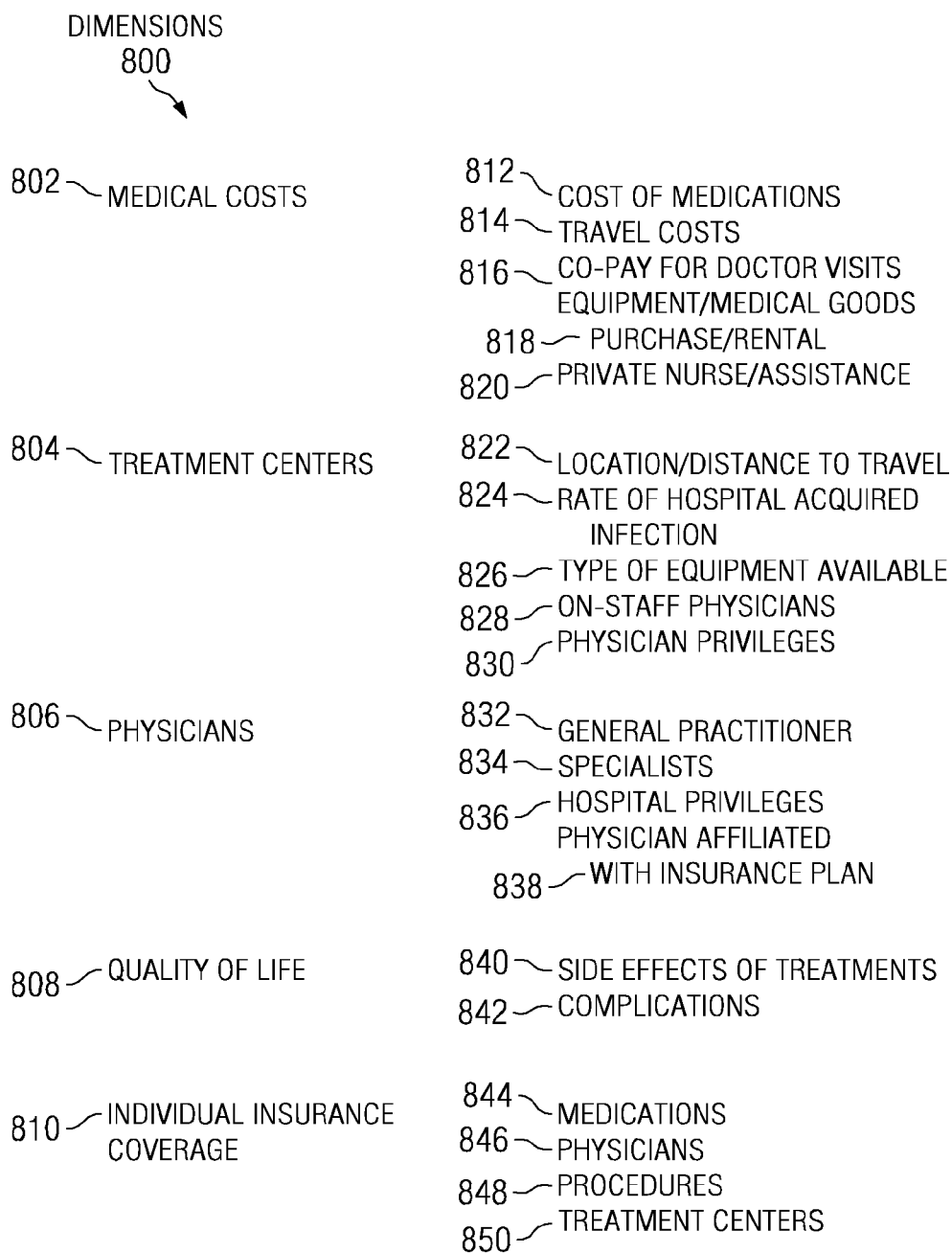
FIG. 8 is a block diagram illustrating dimensions that are used to optimize pharmaceutical treatment plans in accordance with an illustrative embodiment.

FIG. 8 is a block diagram illustrating dimensions that are used to optimize pharmaceutical treatment plans in accordance with an illustrative embodiment. Dimensions 800 is a table of possible dimensions that may be selected by a user for optimizing pharmaceutical treatment plans, such as set of dimensions 335 in FIG. 3.

Medical costs 802 include a sub-dimension for minimizing the costs of treatments for the target individual. A user may specify sub-dimensions of medical costs 802, such as costs of medications 812, travel costs 814, co-pay for doctor visits 816, equipment/durable medical goods purchase and/or rental 818, and/or private nurse/assistance 820. If a user selects medical costs 802, the pharmaceutical treatment plan generator will optimize the pharmaceutical treatment plan to reduce costs for medications, travel to medical centers to receive treatment, co-pay, costs of durable medical goods, and the costs of any private nursing care. However, if the user specifies sub-dimension 812, the pharmaceutical treatment plan generator will only optimize the treatment plan to minimize the costs of medications, such as over-the-counter drugs and prescription drugs.

Treatment centers 804 includes sub-dimensions location/distance to travel 822 to the treatment center, rate of hospital acquired infection 824, type of equipment available 826, on-staff physicians 828, and physician privileges 830. If a user specifies only sub-dimensions 822, 824, and 830, the pharmaceutical treatment plan generator will only optimize the treatment plan to select a treatment center that minimizes the distance the target individual travels, minimizes the rate of hospital acquired infections occurring at the selected treatment center, and maximizes the number of the target individual's physicians that have privileges at the treatment center.

Physicians 806 is a dimension for optimizing physicians chosen by the target individual to administer medications and treatments, such as vaccinations, blood tests, and any other necessary procedures. Sub-dimensions may include general practitioners 832, specialists 834, hospital privileges 836, and physicians affiliated with insurance plan options 838. Thus, if a user selects sub-dimension physicians affiliated with insurance plan options 838, the pharmaceutical treatment plan generator will select physicians to administer treatments to maximize the physicians covered under the target individual's existing health insurance plan and/or covered under a health insurance plan option that may be selected by the target individual in the future time period.

Quality of life 808 minimizes side effects of treatments 840 and complications 842 associated with treatments. Individual insurance coverage 810 is used to optimize selection of a health insurance plan option that maximizes the medications 844, physicians 846, procedures 848, and treatment centers 850 typically used or preferred by the target individual that are covered by the health insurance plan options.

The dimensions shown in FIG. 8 are only examples of dimensions. Additional dimensions not shown in FIG. 8 may also be used without departing from the spirit and scope of the embodiments. For example, a dimension could include maximizing drugs that are Food and Drug Administration (FDA) approved and currently available. In addition, any number of dimensions and sub-dimensions may be used to optimize a treatment plan. The embodiments are not limited to using only two or three dimensions.

Figure 9:
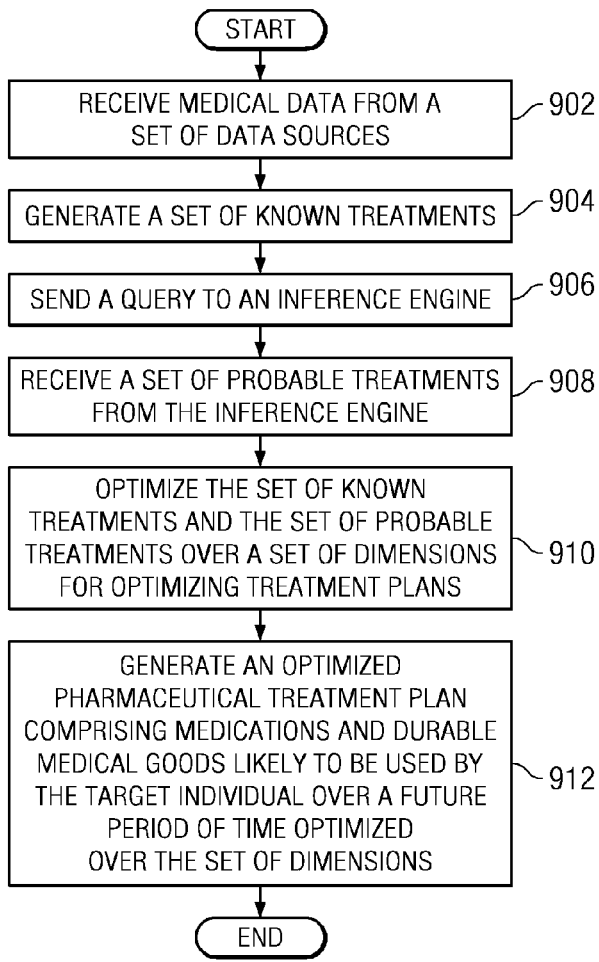
FIG. 9 is a flowchart of a process for generating an optimized pharmaceutical treatment plan in accordance with an illustrative embodiment.

Turning now to FIG. 9, a flowchart of a process for generating an optimized pharmaceutical treatment plan is shown in accordance with an illustrative embodiment. The process in FIG. 9 is implemented by software for generating optimized pharmaceutical treatment plans, such as pharmaceutical treatment plan generator 336 in FIG. 3.

The process begins by receiving medical data from a set of data sources (step 902). A set of known treatments for the target individual over a future period of time is generated based on an analysis of the medical data associated with a target individual (step 904).

A query is sent to an inference engine (step 906). In this example, the query is a request for inferences associated with possible treatments that are likely to be needed by the target individual and the probabilities that those inferences are correct. A set of probable treatments of the target individual is received from the probability engine (step 908).

The set of known treatments and the set of probable treatments are optimized over a set of dimensions for optimizing treatment plans, such as, without limitation, dimensions 800 in FIG. 8 (step 910). An optimized pharmaceutical treatment plan is generated for the target individual (step 912) with the process terminating thereafter. The optimized pharmaceutical treatment plan comprises medications and durable medical goods that are known to be used by the target individual and medications and durable medical goods that are likely to be used by the target individual over the future period of time. The optimized pharmaceutical treatment plan is optimized over a set of dimensions associated with the set of known treatments and the set of probable treatments to create a treatment plan that is optimized for the specific target individual and the selected dimensions.

Figure 10:
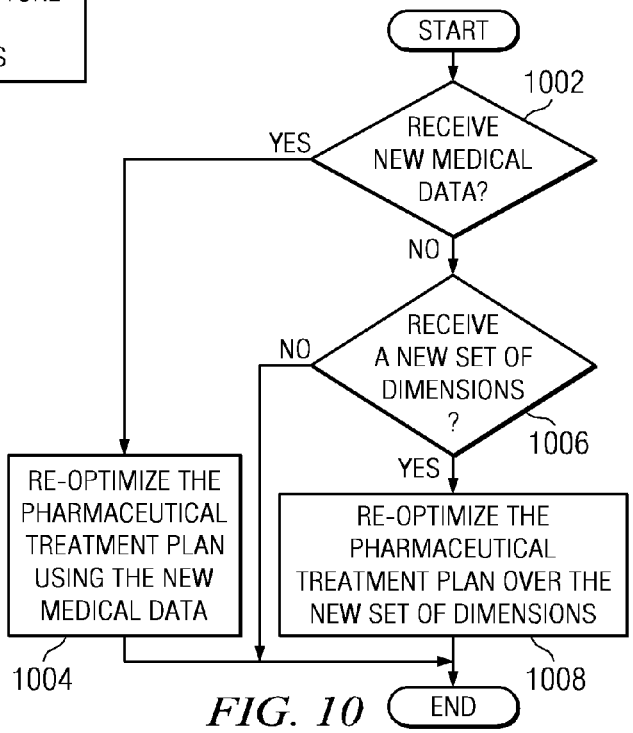
FIG. 10 is a flowchart of a process for re-optimizing a pharmaceutical treatment plan in accordance with an illustrative embodiment.

FIG. 10 is a flowchart of a process for re-optimizing a pharmaceutical treatment plan in accordance with an illustrative embodiment. The process in FIG. 10 is implemented by software for generating optimized pharmaceutical treatment plans, such as pharmaceutical treatment plan generator 336 in FIG. 3.

The process begins by making a determination as to whether new medical data associated with the individual is received (step 1002). In response to receiving new medical data associated with the target individual at step 1002, the process re-optimizes the pharmaceutical treatment plan to generate a new pharmaceutical treatment plan (step 1004). The new pharmaceutical treatment plan is generated using the new medical data. This step may be performed by processing the new medical data in accordance with steps 902-912 in FIG. 9.

Returning to step 1002, if new medical data is not received, the process makes a determination as to whether a new set of dimensions is received (step 1006). For example, a user may select to generate a pharmaceutical treatment plan that is optimized by cost. The user may then select a new set of dimensions to create a new pharmaceutical treatment plan that is optimized to produce the best quality of life for the target individual. If a new set of dimensions is received, the process re-optimizes the pharmaceutical treatment plan to form a new pharmaceutical treatment plan (step 1008) with the process terminating thereafter. The new pharmaceutical treatment plan is optimized across the new dimensions to produce a treatment plan having medicines and durable medical goods known and likely to be needed by the target individual that are optimized across the new dimensions.

In the example, if the first pharmaceutical treatment plan was optimized for cost, the first treatment plan may have included generic brand medicines and treatment centers that are located close to the target individual's home, school, or work place. If the treatment plan is re-optimized with new dimensions for quality of life, a second pharmaceutical treatment plan is generated that has drugs and treatment centers that may be more expensive but that are anticipated to cause fewer negative side effects.

Thus, according to one embodiment of the present invention, a computer implemented method is provided for generating optimized pharmaceutical treatment plans for an individual. Medical data associated with a target individual is analyzed. A set of known treatments to be used by the target individual over a future period of time is generated. The set of known treatments comprises medications and durable medical goods known to be needed by the target individual over the future period of time. An actual use of the treatments in the set of known treatments by the target individual during the future period of time is substantially certain. A query is sent to an inference engine requesting inferences associated with possible treatments that are likely to be needed by the target individual. A set of probable treatments of the target individual is received. The set of probable treatments comprises medications and durable medical goods that are likely to be needed by the target individual during the future period of time. The actual use of the treatments in the set of probable treatments by the target individual during the future period of time is uncertain.

An optimized pharmaceutical treatment plan for the target individual is generated. The optimized pharmaceutical treatment plan comprises medications and durable medical goods that are likely to be used by the target individual over the future period of time. The optimized pharmaceutical treatment plan is optimized over a set of dimensions associated with the set of known treatments and the set of probable treatments.

The pharmaceutical treatment plan generator permits an individual to anticipate expected consumption of pharmaceuticals, durable medical devices, and other medical treatments during any given year. The individual can use this information to optimize the medical treatments selected by the individual and/or the individual's health care providers. The individual can also use this information to select health insurance plans that will maximize the coverage provided for the pharmaceuticals, durable medical goods, and other treatments expected to be used by the individual in the future to reduce the health care costs and optimize treatment.

For example, if the optimized pharmaceutical treatment plan indicates that an individual is unlikely to require many treatments and/or the treatments are inexpensive, the individual may choose a lower end health insurance plan with less coverage but a cheaper premium and/or lower co-pay. If the treatment plan indicates the individual will require substantial treatments, the individual can select a health insurance plan optimized to best cover the treatments that will probably be required by the individual. Patients can also be coalesced into cohort groups and used to draw appropriate inferences from the cohort groups across multiple dimensions and over time.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes, but is not limited to, firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disc and an optical disc. Current examples of optical discs include compact disc-read only memory (CD-ROM), compact disc-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. Computer implemented method for generating optimized pharmaceutical treatment plans for an individual, the computer implemented method comprising:

analyzing, using a processor, medical data associated with a target individual to generate a set of known treatments of the target individual over a future period of time, wherein the set of known treatments comprises medications and durable medical goods known to be needed by the target individual over the future period of time, and wherein an actual use of the treatments in the set of known treatments by the target individual during the future period of time is substantially certain, and further wherein the medical data includes results of tests performed on the target individual;

responsive to a query to an inference engine requesting inferences associated with possible treatments that are likely to be needed by the target individual, receiving a set of probable treatments of the target individual, wherein the set of probable treatments comprises medications and durable medical goods that are likely to be needed by the target individual during the future period of time, and wherein an actual use of the treatments in the set of probable treatments by the target individual during the future period of time is uncertain; and generating an optimized pharmaceutical treatment plan for the target individual, wherein the optimized pharmaceutical treatment plan comprises medications and durable medical goods that are likely to be used by the target individual over the future period of time, and wherein the optimized pharmaceutical treatment plan is optimized over a set of dimensions associated with the set of known treatments and the set of probable treatments; and wherein the set of dimensions includes a first set of information about a plurality of treatment centers and a second set of information about a first plurality of physicians;

wherein the first set of information about the plurality of treatment centers includes a distance of each one of the plurality of treatment centers to the target individual, a rate of hospital acquired infections that have occurred at each one of the plurality of treatment centers, a list of equipment available at each one of the plurality of treatment centers, and a list of a second plurality of physicians that have privileges at each one of the plurality of treatment centers;

wherein the second set of information about the first plurality of physicians includes information about a third plurality of physicians that are specialists, a fourth plurality of physicians that are general practitioners, hospital privileges for each one of the first plurality of physicians, and a fifth plurality of physicians that are affiliated with each one of a plurality of different insurance plans;

wherein the optimized pharmaceutical treatment plan is optimized using the first set of information in response to a receipt, from a user, of a selection of the first set of information; and wherein the optimized pharmaceutical treatment plan is optimized using the second set of information in response to a receipt, from the user, of a selection of the second set of information.

2. The computer implemented method of claim 1 further comprising:
receiving the medical data associated with a target individual from a federated database server, wherein the federated database server is coupled to a plurality of data sources.

3. The computer implemented method of claim 1 further comprising:
generating a set of multidimensional cohorts, wherein the set of probable treatments is generated using treatments provided to cohorts having similar characteristics as the target individual.

4. The computer implemented method of claim 1 wherein the optimized pharmaceutical treatment plan comprises an optimized individual insurance coverage plan corresponding to the set of known treatments and the set of probable treatments.

5. The computer implemented method of claim 1 further comprising:
wherein the set of dimensions further comprises a third set of information about medical costs, a fourth set of information about quality of life, and a fifth set of information about individual insurance coverage;
wherein the third set of information includes information about cost of medications travel costs, co-pay for doctor visits, equipment rental, and nursing assistance;
wherein the fourth set of information includes information about side effects of treatments and complications; and
wherein the fifth set of information includes information about covered medications, covered physicians, covered procedures, and covered treatment centers.

6. The computer implemented method of claim 1 further comprising:
receiving the medical data associated with a target individual from a user.

7. The computer implemented method of claim 1 further comprising:
identifying known complications and side effects of treatments in the set of known treatments; and
generating treatments for the known complications and the known side effects of the treatments in the set of known treatments to form a subset of probable treatments in the set of probable treatments.

8. The computer implemented method of claim 1 further comprising:
analyzing the medical data to generate a set of data structures for storing the medical data;
generating a set of cohorts based on the set of data structures, wherein a cohort in the set of cohorts comprises objects sharing a common characteristic; and
identifying cohorts of interest in the set of cohorts, wherein a cohort of interest is a cohort sharing one or more common characteristics with the target individual; and
optimizing treatment plans to generate the optimized pharmaceutical treatment plan based on medical data associated with the cohorts of interest.

9. The computer implemented method of claim 1 further comprising:
responsive to receiving new medical data associated with the target individual, re-optimizing the pharmaceutical treatment plan to generate a new pharmaceutical treatment plan, wherein the new pharmaceutical treatment plan is generated using the new medical data; and
responsive to receiving a new set of dimensions, re-optimizing the pharmaceutical treatment plan to form a new pharmaceutical treatment plan, wherein the new pharmaceutical treatment plan is optimized across the new dimensions.

10. A computer program product for generating optimized pharmaceutical treatment plans for an individual, the computer program product comprising:
a non-transitory computer readable medium;
program code stored on the computer readable medium for analyzing medical data associated with a target individual to generate a set of known treatments of the target individual over a future period of time, wherein the set of known treatments comprises medications and durable medical goods known to be needed by the target individual over the future period of time, and wherein an actual use of the treatments in the set of known treatments by the target individual during the future period of time is substantially certain, and further wherein the medical data includes results of tests performed on the target individual;
program code stored on the computer readable medium for receiving a set of probable treatments of the target individual in response to a query to an inference engine requesting inferences associated with possible treatments that are likely to be needed by the target individual, wherein the set of probable treatments comprises medications and durable medical goods that are likely to be needed by the target individual during the future period of time, and wherein an actual use of the treatments in the set of probable treatments by the target individual during the future period of time is uncertain;
program code stored on the computer readable medium for generating an optimized pharmaceutical treatment plan for the target individual, wherein the optimized pharmaceutical treatment plan comprises medications and durable medical goods that are likely to be used by the target individual over the future period of time, and wherein the optimized pharmaceutical treatment plan is optimized over a set of dimensions associated with the set of known treatments and the set of probable treatments;
wherein the set of dimensions includes a first set of information about a plurality of treatment centers and a second set of information about a first plurality of physicians;
wherein the first set of information about the plurality of treatment centers includes a distance of each one of the plurality of treatment centers to the target individual, a rate of hospital acquired infections that have occurred at each one of the plurality of treatment centers, a list of equipment available at each one of the plurality of treatment centers, and a list of a second plurality of physicians that have privileges at each one of the plurality of treatment centers;
wherein the second set of information about the first plurality of physicians includes information about a third plurality of physicians that are specialists, a fourth plurality of physicians that are general practitioners, hospital privileges for each one of the first plurality of physicians, and a fifth plurality of physicians that are affiliated with each one of a plurality of different insurance plans;
wherein the optimized pharmaceutical treatment plan is optimized using the first set of information in response to a receipt, from a user, of a selection of the first set of information; and wherein the optimized pharmaceutical treatment plan is optimized using the second set of information in response to a receipt, from the user, of a selection of the second set of information.

11. The computer program product of claim 10 further comprising:
program code stored on the computer readable medium for receiving the medical data associated with a target individual from a federated database server, wherein the federated database server is coupled to a plurality of data sources.

12. The computer program product of claim 10 further comprising:
program code stored on the computer readable medium for generating a set of multidimensional cohorts, wherein the set of probable treatments is generated using treatments provided to cohorts having similar characteristics as the target individual.

13. The computer program product of claim 10 wherein the optimized pharmaceutical treatment plan comprises an optimized individual insurance coverage plan corresponding to the set of known treatments and the set of probable treatments.

14. The computer program product of claim 10 further comprising:
program code stored on the computer readable medium for receiving a selection of the set of dimensions, wherein the set of dimensions further comprises a third set of information about medical costs, a fourth set of information about quality of life, and a fifth set of information about individual insurance coverage;
wherein the third set of information includes information about cost of medications travel costs, co-pay for doctor visits, equipment rental, and nursing assistance;
wherein the fourth set of information includes information about side effects of treatments and complications; and
wherein the fifth set of information includes information about covered medications, covered physicians, covered procedures, and covered treatment centers.

15. The computer program product of claim 10 further comprising:
program code stored on the computer readable medium for receiving the medical data associated with a target individual from a user.

16. The computer program product of claim 10 further comprising:
program code stored on the computer readable medium for identifying known complications and side effects of treatments in the set of known treatments; and
program code stored on the computer readable medium for generating treatments for the known complications and the known side effects of the treatments in the set of known treatments to form a subset of probable treatments in the set of probable treatments.

17. The computer program product of claim 10 further comprising:
program code stored on the computer readable medium for analyzing the medical data to generate a set of data structures for storing the medical data;
program code stored on the computer readable medium for generating a set of cohorts based on the set of data structures, wherein a cohort in the set of cohorts comprises objects sharing a common characteristic; and
program code stored on the computer readable medium for identifying cohorts of interest in the set of cohorts, wherein a cohort of interest is a cohort sharing one or more common characteristics with the target individual; and
program code stored on the computer readable medium for optimizing treatment plans to generate the optimized pharmaceutical treatment plan based on medical data associated with the cohorts of interest.

18. The computer program product of claim 10 further comprising:
program code stored on the computer readable medium for re-optimizing the pharmaceutical treatment plan to generate a new pharmaceutical treatment plan in response to receiving new medical data associated with the target individual, wherein the new pharmaceutical treatment plan is generated using the new medical data; and
program code stored on the computer readable medium for re-optimizing the pharmaceutical treatment plan to form a new pharmaceutical treatment plan in response to receiving a new set of dimensions, wherein the new pharmaceutical treatment plan is optimized across the new dimensions.

19. An apparatus comprising:
a bus system;
a communications system coupled to the bus system;
a memory connected to the bus system, wherein the memory includes computer usable program code; and
processing unit coupled to the bus system, wherein the processing unit executes the computer usable program code to analyze medical data associated with a target individual to generate a set of known treatments of the target individual over a future period of time, wherein the set of known treatments comprises medications and durable medical goods known to be needed by the target individual over the future period of time, and wherein an actual use of the treatments in the set of known treatments by the target individual during the future period of time is substantially certain, and further wherein the medical data includes results of tests performed on the target individual; receiving a set of probable treatments of the target individual in response to a query to an inference engine requesting inferences associated with possible treatments that are likely to be needed by the target individual, wherein the set of probable treatments comprises medications and durable medical goods that are likely to be needed by the target individual during the future period of time, and wherein an actual use of the treatments in the set of probable treatments by the target individual during the future period of time is uncertain; and generate an optimized pharmaceutical treatment plan for the target individual, wherein the optimized pharmaceutical treatment plan comprises medications and durable medical goods that are likely to be used by the target individual over the future period of time, wherein the optimized pharmaceutical treatment plan is optimized over a set of dimensions associated with the set of known treatments and the set of probable treatments; wherein the set of dimensions includes a first set of information about a plurality of treatment centers and a second set of information about a first plurality of physicians; wherein the first set of information about the plurality of treatment centers includes a distance of each one of the plurality of treatment centers to the target individual, a rate of hospital acquired infections that have occurred at each one of the plurality of treatment centers, a list of equipment available at each one of the plurality of treatment centers, and a list of a second plurality of physicians that have privileges at each one of the plurality of treatment centers; wherein the second set of information about the first plurality of physicians includes information about a third plurality of physicians that are specialists, a fourth plurality of physicians that are general practitioners, hospital privileges for each one of the first plurality of physicians, and a fifth plurality of physicians that are affiliated with each one of a plurality of different insurance plans; wherein the optimized pharmaceutical treatment plan is optimized using the first set of information in response to a receipt, from a user, of a selection of the first set of information; and wherein the optimized pharmaceutical treatment plan is optimized using the second set of information in response to a receipt, from the user, of a selection of the second set of information.

20. The apparatus of claim 19 wherein the processor unit further executes the computer usable program code to receive the medical data associated with a target individual from a federated database server, wherein the federated database server is coupled to a plurality of data sources.

21. The apparatus of claim 19 wherein the processor unit further executes the computer usable program code to generate a set of multidimensional cohorts, wherein the set of probable treatments is generated using treatments provided to cohorts having similar characteristics as the target individual.

22. The apparatus of claim 19 wherein the processor unit further executes the computer usable program code to receive a selection of the set of dimensions, wherein the set of dimensions comprises at least one of medical costs, treatment centers, physicians, quality of life, and individual insurance coverage.

23. A data processing system for generating optimized pharmaceutical treatment plans for an individual, the data processing system comprising:

a data storage device comprising a set of known treatments associated with a target individual, wherein the set of known treatments comprises medications and durable medical goods known to be needed by the target individual over a future period of time, and wherein an actual use of the treatments in the set of known treatments by the target individual during the future period of time is substantially certain, and further wherein the medical data includes results of tests performed on the target individual;

a pharmaceutical treatment plan generator, wherein the pharmaceutical treatment plan generator generators retrieves a set of probable treatments associated with the individual, wherein the set of probable treatments comprises medications and durable medical goods that are likely to be needed by the target individual during the future period of time, and wherein an actual use of the treatments in the set of probable treatments by the target individual during the future period of time is uncertain, and wherein the pharmaceutical treatment plan generator generates an optimized pharmaceutical treatment plan for the target individual using the set of known treatments and the set of probable treatments, wherein the optimized pharmaceutical treatment plan comprises medications and durable medical goods that are known to be needed by the target individual and medications and durable medical goods that are likely to be used by the target individual over the future period of time, and wherein the optimized pharmaceutical treatment plan is optimized over a set of dimensions associated with the set of known treatments and the set of probable treatments; and wherein the set of dimensions includes a first set of information about a plurality of treatment centers and a second set of information about a first plurality of physicians;

wherein the first set of information about the plurality of treatment centers includes a distance of each one of the plurality of treatment centers to the target individual, a rate of hospital acquired infections that have occurred at each one of the plurality of treatment centers, a list of equipment available at each one of the plurality of treatment centers, and a list of a second plurality of physicians that have privileges at each one of the plurality of treatment centers;

wherein the second set of information about the first plurality of physicians includes information about a third plurality of physicians that are specialists, a fourth plurality of physicians that are general practitioners, hospital privileges for each one of the first plurality of physicians, and a fifth plurality of physicians that are affiliated with each one of a plurality of different insurance plans;

wherein the optimized pharmaceutical treatment plan is optimized using the first set of information in response to a receipt, from a user, of a selection of the first set of information; and wherein the optimized pharmaceutical treatment plan is optimized using the second set of information in response to a receipt, from the user, of a selection of the second set of information.

24. The data processing system of claim 23 further comprising:

an inference engine, wherein the inference engine receives a query requesting inferences associated with possible treatments that are likely to be needed by the target individual, and wherein the inference engine generates the set of probable treatments for the target individual.

25. The data processing system of claim 23 further comprising:

a target data analysis component, wherein the target data analysis component analyzes medical data associated with a target individual to generate a set of known treatments for the target individual over the future period of time.

* * * * *